United States Patent
Iida et al.

(10) Patent No.: US 11,464,881 B2
(45) Date of Patent: Oct. 11, 2022

(54) FLUID STERILIZATION APPARATUS AND FLUID STERILIZATION SYSTEM

(71) Applicant: Toshiba Lighting & Technology Corporation, Yokosuka (JP)

(72) Inventors: Seiya Iida, Ehime-ken (JP); Takeo Kato, Ehime-ken (JP); Naoto Sakurai, Ehime-ken (JP)

(73) Assignee: Toshiba Lighting & Technology Corporation, Yokosuka (JP)

( * ) Notice: Subject to any disclaimer, the term of this patent is extended or adjusted under 35 U.S.C. 154(b) by 8 days.

(21) Appl. No.: 17/166,708

(22) Filed: Feb. 3, 2021

(65) Prior Publication Data
US 2021/0283294 A1  Sep. 16, 2021

(30) Foreign Application Priority Data

Mar. 16, 2020  (JP) .............................. JP2020-045009

(51) Int. Cl.
| | | |
|---|---|---|
| *A61L 2/26* | (2006.01) | |
| *C02F 1/32* | (2006.01) | |
| *A61L 2/10* | (2006.01) | |
| *A61L 9/20* | (2006.01) | |

(52) U.S. Cl.
CPC ................... *A61L 2/26* (2013.01); *A61L 2/10* (2013.01); *A61L 9/20* (2013.01); *C02F 1/325* (2013.01); *A61L 2202/11* (2013.01); *A61L 2202/122* (2013.01); *A61L 2209/12* (2013.01); *C02F 2201/3222* (2013.01); *C02F 2201/3228* (2013.01); *C02F 2303/04* (2013.01)

(58) Field of Classification Search
None
See application file for complete search history.

(56) References Cited

U.S. PATENT DOCUMENTS

| | | | |
|---|---|---|---|
| 10,669,167 B2* | 6/2020 | Ochi | C02F 1/32 |
| 2017/0112952 A1* | 4/2017 | Kato | A61L 2/10 |
| 2019/0055139 A1* | 2/2019 | Ochi | C02F 1/325 |
| 2019/0256380 A1* | 8/2019 | Ochi | C02F 1/32 |
| 2020/0071196 A1* | 3/2020 | Ochi | C02F 1/325 |

FOREIGN PATENT DOCUMENTS

| | | | | | |
|---|---|---|---|---|---|
| JP | 2015126162 A | * | 7/2015 | ........... | B08B 7/0057 |
| JP | 2018-069166 A | | 5/2018 | | |
| JP | 2018069166 A | * | 5/2018 | ............... | C02F 1/32 |
| WO | WO-2020091318 A1 | * | 5/2020 | ............... | A61L 9/20 |

* cited by examiner

*Primary Examiner* — Andrew Smyth
(74) *Attorney, Agent, or Firm* — Banner & Witcoff, Ltd.

(57) ABSTRACT

A fluid sterilization apparatus according to an embodiment includes a tubular portion; a supply head provided at one end of the tubular portion; a discharge head provided at the other end of the tubular portion; a holder provided on the discharge head; a window provided on the discharge head and one surface of which is exposed to a flow path provided in the discharge head; a board provided on a surface of the holder on a side of the window; a light-emitting element provided on the board and allowed to irradiate the window with ultraviolet rays; and a heat insulating portion which is provided between the discharge head and the holder and has a lower thermal conductivity than a thermal conductivity of the holder.

20 Claims, 4 Drawing Sheets

|  | Ts |
|---|---|
| COMPARATIVE EXAMPLE (HEAT INSULATING PORTION 10a IS NOT PROVIDED) | 60°C |
| EXAMPLE (HEAT INSULATING PORTION 10a IS PROVIDED) | 42°C |

FIG. 3

FLUID STERILIZATION APPARATUS AND FLUID STERILIZATION SYSTEM

CROSS-REFERENCE TO RELATED APPLICATIONS

This application is based upon and claims the benefit of priority from Japanese Patent Application No. 2020-045009, filed on Mar. 16, 2020; the entire contents of which are incorporated herein by reference.

FIELD

Embodiments described herein relate generally to a fluid sterilization apparatus and a fluid sterilization system.

BACKGROUND

There is a fluid sterilization apparatus that sterilizes a fluid such as water by irradiating the fluid with ultraviolet rays. As a light source provided in the fluid sterilization apparatus, an ultraviolet light-emitting diode (Ultraviolet LED) is used.

Here, the LED has a temperature characteristic. For example, when a temperature of the LED exceeds a maximum junction temperature, there is concern that a luminous flux drop, non-lighting, etc. may occur, or the life of the LED may be shortened. For this reason, there is a proposed technology for water-cooling a block to which a board having the LED mounted thereon is attached.

However, when the fluid sterilization apparatus sterilizes a fluid having a high temperature, heat of the fluid may be transferred to the block to which the board having the LED mounted thereon is attached, and the temperature of the LED may become high. In this case, increasing capacity of a cooling apparatus leads to an increase in size and cost of the fluid sterilization apparatus.

Therefore, there is a desire for developing a technology that can suppress a temperature rise of a light source using a simple configuration.

DESCRIPTION OF THE DRAWINGS

FIG. 3 is a table for showing effects of heat insulating portions.

DETAILED DESCRIPTION

Figure 1:
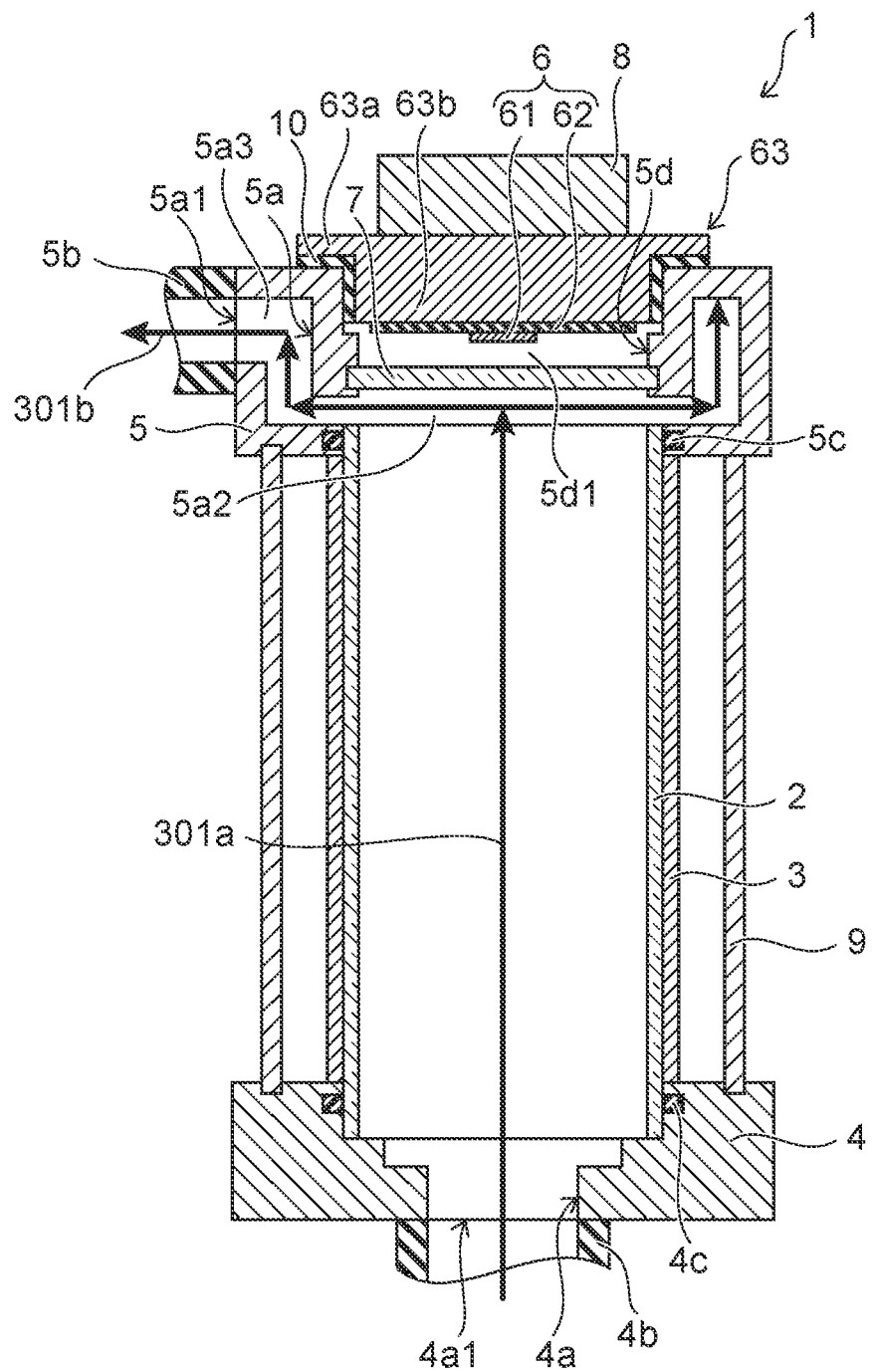
FIG. 1 is a schematic cross-sectional view for illustrating a fluid sterilization apparatus according to the present embodiment.

A fluid sterilization apparatus according to an embodiment includes a tubular portion; a supply head provided at one end of the tubular portion; a discharge head provided at the other end of the tubular portion; a holder provided on the discharge head; a window provided on the discharge head and one surface of which is exposed to a flow path provided in the discharge head; a board provided on a surface of the holder on a side of the window; a light-emitting element provided on the board and allowed to irradiate the window with ultraviolet rays; and a heat insulating portion which is provided between the discharge head and the holder and has a lower thermal conductivity than a thermal conductivity of the holder.

Hereinafter, embodiments will be illustrated with reference to the drawings. Note that in each drawing, similar components are denoted by the same reference numerals and detailed description thereof will be omitted as appropriate.

(Fluid Sterilization Apparatus 1)

For example, a fluid sterilization apparatus 1 according to the present embodiment can be used to sterilize a fluid having a temperature higher than room temperature (for example, water, air at 40° C. or higher, etc.). However, the fluid sterilization apparatus 1 can also be used to sterilize a fluid at room temperature or lower (for example, water, air at 25° C. or lower, etc.). In the following, as an example, a description will be given of a case where the fluid sterilization apparatus 1 is used for sterilizing a liquid having a temperature of 40° C. or higher.

FIG. 1 is a schematic cross-sectional view for illustrating the fluid sterilization apparatus 1 according to the present embodiment.

As illustrated in FIG. 1, the fluid sterilization apparatus 1 can be provided with a tubular portion 2, a reflective portion 3, a supply head 4, a discharge head 5, a light source 6, a window 7, a cooling portion 8, a cover 9, and a heat insulating portion 10.

The tubular portion 2 has a tubular shape, and ends on both sides thereof are open. For example, the tubular portion 2 can be a cylindrical tube. A material of the tubular portion 2 is not particularly limited as long as the material is resistant to ultraviolet rays and a fluid 301a subjected to sterilization. For example, the material of the tubular portion 2 may be quartz or a fluororesin such as polytetrafluoroethylene (PTFE).

The reflective portion 3 can be provided on an outer surface of the tubular portion 2. The tubular portion 2 may be formed of a material that transmits ultraviolet rays, such as quartz. When a part of the ultraviolet rays emitted from the light source 6 passes through the tubular portion 2 and leaks to the outside, the processing capacity of the fluid sterilization apparatus 1 is lowered. When the reflective portion 3 is provided on the outer surface of the tubular portion 2, the ultraviolet rays directed to the outside of the tubular portion 2 can be reflected toward the inside of the tubular portion 2. For this reason, the utilization efficiency of the ultraviolet rays emitted from the light source 6 can be improved, and thus the number of light-emitting elements 61 can be reduced. When the number of light-emitting elements 61 is reduced, the size and cost of the light source 6 can be reduced.

The reflective portion 3 can be formed of a material having a high reflectance of ultraviolet rays. Examples of the material of the reflective portion 3 may include aluminum, an aluminum alloy, and silicon dioxide. The reflective portion 3 has a plate shape and can be attached to the outer surface of the tubular portion 2. Further, the reflective portion 3 having a shape of a film can be formed on the outer surface of the tubular portion 2 using a film forming method such as a sputtering method or an evaporation method.

Further, even though a case where the reflective portion 3 is provided on the outer surface of the tubular portion 2 is illustrated, the reflective portion 3 may be provided on an inner side face of the tubular portion 2. However, when corrosion, etc. occurs due to contact between the reflective portion 3 and the fluid 301a (for example, water) before sterilization, or when the material of the reflective portion 3 melts out, the reflective portion is preferably formed on the outer surface of the tubular portion 2.

Further, the reflective portion 3 can be omitted. For example, when the tubular portion 2 is formed of a material that reflects ultraviolet rays (for example, a white inorganic material or a white resin), the reflective portion 3 can be omitted.

The supply head 4 is provided at one end of the tubular portion 2. For example, the supply head 4 has a cylindrical shape and has a hole 4a penetrating between one end face and the other end face. One opening of the hole 4a is connected to an internal space of the tubular portion 2. The other opening of the hole 4a serves as a supply port 4a1. For example, a fluid supply unit (for example, a tank 101, a heater 102, a pump 103, and a flow rate control valve 104) capable of supplying the fluid 301a having a temperature higher than room temperature (25° C.) can be connected to the supply port 4a1 via a pipe 4b (see FIG. 4).

Further, a seal member 4c such as an O-ring can be provided on an inner wall of the hole 4a. The seal member 4c is sealed so that a space between the supply head 4 and the tubular portion 2 is liquid-tight. Further, a filter, a current plate, etc. can be provided inside the hole 4a.

A material of the supply head 4 is not particularly limited as long as the material is resistant to the fluid 301a and ultraviolet rays. The material of the supply head 4 can be, for example, a metal such as stainless steel.

The discharge head 5 is provided at the other end of the tubular portion 2. For example, the discharge head 5 has a cylindrical shape and has holes 5a and 5d. One opening of the hole 5a is connected to the internal space of the tubular portion 2. The other opening of the hole 5a serves as a discharge port 5a1 provided on a side face of the discharge head 5. A tank 105, a cleaning device, etc. can be connected to the discharge port 5a1 via a pipe 5b (see FIG. 4).

Further, a seal member 5c such as an O-ring can be provided on an inner wall of the hole 5a. The seal member 5c is sealed so that a space between the discharge head 5 and the tubular portion 2 is liquid-tight.

A material of the discharge head 5 is not particularly limited as long as the material is resistant to a fluid 301b after sterilization and ultraviolet rays. The material of the discharge head 5 can be, for example, a metal such as stainless steel.

As illustrated in FIG. 1, the hole 5a is a bent flow path. The hole 5a has a flow path 5a2 substantially parallel to an end face of the discharge head 5 on the tubular portion 2 side, and a flow path 5a3 extending in an axial direction of the discharge head 5.

The flow path 5a2 is open to the end face of the discharge head 5 on the tubular portion 2 side. Further, the window 7 is exposed on an inner wall of the flow path 5a2. The flow path 5a2 can be, for example, a disk-shaped space.

One end of the flow path 5a3 is connected to the vicinity of a peripheral edge of the flow path 5a2. The discharge port 5a1 is connected to the other end of the flow path 5a3. The flow path 5a3 can be, for example, a cylindrical space.

As illustrated in FIG. 1, the fluid 301a supplied to the inside of the tubular portion 2 via the supply head 4 is supplied to the inside of the flow path 5a2. The fluid 301a supplied to the inside of the flow path 5a2 hits the window 7 and flows along a surface of the window 7 toward a peripheral edge side of the window 7. In this instance, the fluid 301a is sterilized by ultraviolet rays emitted through the window 7. The sterilized fluid 301b is discharged from the discharge port 5a1 via the flow path 5a3.

When the hole 5a is a flow path bent in this way, the flow velocity of the fluid 301a flowing inside the flow path 5a2 can be slowed down. For this reason, the residence time of the fluid 301a in a region where the window 7 is exposed can be lengthened, so that the bactericidal effect can be improved.

Note that a part of ultraviolet rays emitted to the flow path 5a2 is emitted to the internal space of the tubular portion 2. Further, a part of the ultraviolet rays emitted to the internal space of the tubular portion 2 is reflected by the reflective portion 3. For this reason, the fluid 301a is sterilized in the internal space of the tubular portion 2.

The hole 5d is open to the end face of the discharge head 5 on the opposite side to the tubular portion 2 side and the flow path 5a2.

The light source 6 is detachably provided on the discharge head 5.

The light source 6 has, for example, a light-emitting element 61, a board 62, and a holder 63.

The light-emitting element 61 is provided on the board 62 and can irradiate the window 7 with ultraviolet rays. At least one light-emitting element 61 can be provided. When a plurality of light-emitting elements 61 are provided, the plurality of light-emitting elements 61 can be connected in series. The light-emitting element 61 is not particularly limited as long as the light-emitting element 61 is an element that generates ultraviolet rays. The light-emitting element 61 can be, for example, an LED, a laser diode, etc.

A peak wavelength of the ultraviolet rays emitted from the light-emitting element 61 is not particularly limited as long as the bactericidal effect is obtained. However, when the peak wavelength is 260 nm to 280 nm, the bactericidal effect can be improved. For this reason, it is preferable that the light-emitting element 61 can emit ultraviolet rays having a peak wavelength of 260 nm to 280 nm.

The board 62 has a plate shape and is provided on a surface of the holder 63 on the window 7 side. A wiring pattern can be provided on one surface of the board 62. A material of the board 62 is preferably resistant to ultraviolet rays. The material of the board 62 can be, for example, ceramics such as aluminum oxide. The board 62 may be a metal plate whose surface is covered with an inorganic material (metal core board). When the material of the board 62 is ceramics, etc., or when the board 62 is a metal core board, it is possible to obtain resistance to ultraviolet rays and a high thermal radiation property.

The holder 63 can be detachably provided on the discharge head 5. The light-emitting element 61 has a longer life than that of a discharge lamp, etc. However, the light-emitting efficiency decreases as the lighting time becomes longer. Further, it is also conceivable that the light-emitting element 61 may break down and be turned off. When the holder 63 is detachably provided on the discharge head 5, the light-emitting element 61 can be easily replaced.

The holder 63 may include, for example, a flange 63a and a convex portion 63b. The flange 63a and the convex portion 63b can be integrally formed.

The flange 63a has a plate shape and can be attached to the end face of the discharge head 5 on the opposite side to the tubular portion 2 side. The flange 63a can be attached to the discharge head 5 using, for example, a fastening member such as a screw.

The convex portion 63b is provided on a surface of the flange 63a on the tubular portion 2 side. The board 62 on which the light-emitting element 61 is mounted can be provided on an end face of the convex portion 63b on the tubular portion 2 side. The convex portion 63b has a function of determining a position of the light-emitting element 61 with respect to the discharge head 5. For example, a side face of the convex portion 63b can be brought into contact with an inner wall of the hole 5d of the discharge head 5 via the heat insulating portion 10. In this way, it is possible to determine the position of the light-emitting element 61 with respect to the discharge head 5.

Further, since the hole 5d of the discharge head 5 and the flow path 5a2 are separated by the window 7, the light source 6 can be attached and detached even when the fluid 301a is present in the flow path 5a2. For this reason, maintainability can be improved.

Further, the holder 63 can have a function of releasing heat generated in the light-emitting element 61 to the outside. For this reason, the holder 63 is preferably formed of a material having high thermal conductivity. The holder 63 can be formed of, for example, a metal such as aluminum, copper, or stainless steel. Further, thermal radiation fins may be provided on an end face, a side face of the holder 63 on the opposite side to the light-emitting element 61 side, etc.

The window 7 has a plate shape and is provided on the inner wall of the hole 5d of the discharge head 5 so as to be liquid-tight. That is, the window 7 is provided on the discharge head 5, and one surface of the window 7 is exposed to the flow path 5a2 provided in the discharge head 5. A space 5d1 can be provided between the window 7 and the light-emitting element 61. The window 7 can be formed of a material that is capable of transmitting ultraviolet rays and has resistance to ultraviolet rays and the fluid 301a. The window 7 can be formed of, for example, quartz, a fluororesin that transmits ultraviolet rays, etc.

Further, an antireflection film may be provided on a surface of the window 7 on the light-emitting element 61 side. When the antireflection film is provided, it is possible to prevent the ultraviolet rays emitted from the light-emitting element 61 from being reflected by the window 7 and becoming difficult to irradiate the fluid 301a. That is, it is possible to improve the utilization efficiency of the ultraviolet rays emitted from the light-emitting element 61.

Further, an antifouling film can be provided on the surface of the window 7 on the tubular portion 2 side. The fluid 301a may contain impurities. When impurities adhere to the window 7, it becomes difficult for the ultraviolet rays emitted from the light-emitting element 61 to pass through the window 7. When the antifouling film is provided, it is possible to inhibit the impurities from adhering to the window 7. For this reason, it is possible to suppress the difficulty in irradiating the fluid 301a with ultraviolet rays over time.

The cooling portion 8 can be provided, for example, on the opposite side of the holder 63 from the light-emitting element 61 side. The cooling portion 8 can be, for example, a fan, etc. that supply air to the holder 63. Further, when the holder 63 is provided with thermal radiation fins, the cooling portion 8 can be a fan that supplies air to the thermal radiation fins. Further, for example, the cooling portion 8 may supply a liquid to the flow path provided in the holder 63. That is, the cooling portion 8 may be an air-cooled type or a liquid-cooled type.

Note that the cooling portion 8 can be omitted depending on the number or the heat generation amount of light-emitting elements 61, the temperature or the flow rate of the fluid 301a, etc. However, if the cooling portion 8 is provided, even when the number of light-emitting elements 61, the applied power, etc. are increased, the temperature of the light-emitting element 61 hardly exceeds a maximum junction temperature.

Further, if the cooling portion 8 is provided, even when the temperature of the fluid 301a rises or the flow rate of the fluid 301a having a high temperature increases, the temperature of the light-emitting element 61 hardly exceeds the maximum junction temperature. For this reason, it is possible to extend a range of the fluid 301a that can be handled.

The cover 9 has a tubular shape and can house the tubular portion 2 and the reflective portion 3 in an internal space. A material of the cover 9 is not particularly limited as long as the material has a certain degree of rigidity. The material of the cover 9 can be, for example, a metal such as stainless steel. The cover 9 can be fixed to, for example, the supply head 4 and the discharge head 5. A method of fixing the cover 9 is not particularly limited. For example, one end of the cover 9 can be provided inside a groove provided in the supply head 4, and the other end of the cover 9 can be provided inside a groove provided in the discharge head 5. Further, for example, flanges may be provided at the ends of the cover 9 on both sides, so that one flange may be fixed to the supply head 4 using a screw, etc., and the other flange may be fixed to the discharge head 5 using a screw, etc.

As will be described later, the fluid 301a having a high temperature (for example, the fluid 301a having a temperature of about 40° C. to 90° C.) may be supplied to the fluid sterilization apparatus 1. The heat of the fluid 301a is transferred to the light-emitting element 61 via the window 7. As described above, since there is a space between the window 7 and the light-emitting element 61, heat transfer via the window 7 can be suppressed.

However, the heat of the fluid 301a is transferred to the light-emitting element 61 via the discharge head 5, the holder 63, and the board 62. Since the discharge head 5 and the holder 63 are made of metal, etc., heat can be easily transferred. Further, since the board 62 is formed of ceramics, etc., or is a metal core board, etc., heat can be easily transferred. For this reason, the heat of the fluid 301a is easily transferred to the light-emitting element 61 via the discharge head 5, the holder 63, and the board 62, and the temperature of the light-emitting element 61 may exceed the maximum junction temperature. When the temperature of the light-emitting element 61 exceeds the maximum junction temperature, there is concern that a luminous flux drop, non-lighting, etc. may occur, or the life of the LED may be shortened.

In this case, increasing the capacity of the cooling portion 8 leads to an increase in size and cost of the fluid sterilization apparatus 1.

Therefore, the fluid sterilization apparatus 1 according to the present embodiment is provided with the heat insulating portion 10.

The heat insulating portion 10 can be provided between the discharge head 5 and the holder 63. The heat insulating portion 10 has a lower thermal conductivity than a thermal conductivity of the holder 63. The heat insulating portion 10 can be formed of, for example, a resin such as a phenol resin or a fluororesin. A thickness of the heat insulating portion 10 (distance between the discharge head 5 and the holder 63) can be set to about 1 mm to 3 mm. Further, a hole, a groove, etc. can be provided in the heat insulating portion 10. When the heat insulating portion 10 is provided with the hole, the groove, etc., it is possible to form a region filled with air having a lower thermal conductivity than that of the resin. That is, the heat insulating portion 10 can contain air. For this reason, the overall thermal conductivity of the heat insulating portion 10 can be lowered.

When the heat insulating portion 10 is provided, the heat of the fluid 301a can be inhibited from being transferred from the discharge head 5 to the holder 63, and thus the temperature rise of the light-emitting element 61 can be suppressed.

Figure 2A:
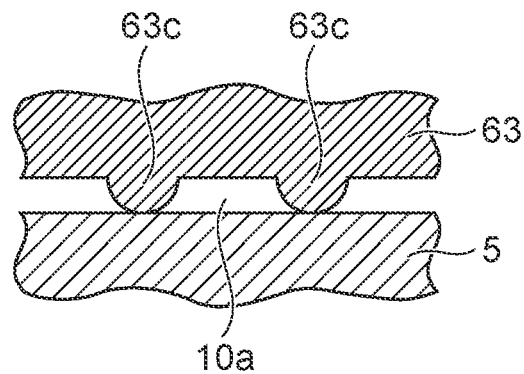
FIGS. 2A to 2C are schematic views for illustrating a heat insulating portion according to another embodiment.
Figure 2B:
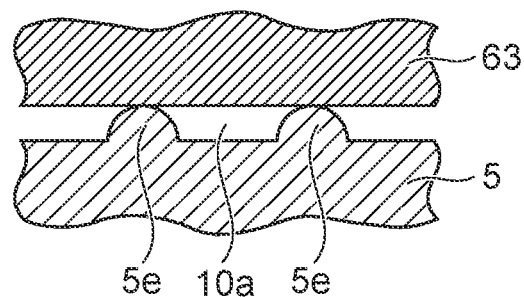
Figure 2C:
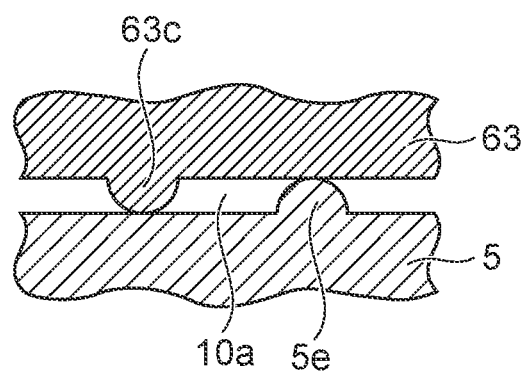

FIGS. 2A to 2C are schematic views for illustrating a heat insulating portion 10a according to another embodiment.

As illustrated in FIGS. 2A to 2C, the heat insulating portion 10a can be a region provided between the discharge head 5 and the holder 63. This region is filled with a gas (for example, air) present in an environment in which the fluid sterilization apparatus 1 is provided. That is, the heat insulating portion 10a can contain air. In general, a thermal conductivity of a gas is lower than a thermal conductivity of a solid such as a resin or metal, and thus the heat of the fluid 301a can be further inhibited from being transferred from the discharge head 5 to the holder 63.

For example, as illustrated in FIG. 2A, a protrusion 63c can be provided on the holder 63, and a tip of the protrusion 63c can be brought into contact with the discharge head 5. That is, the heat insulating portion can be at least one protrusion 63c provided on the holder 63. In this way, it is possible to provide a region containing gas between the discharge head 5 and the holder 63.

The protrusion 63c can maintain a space between the discharge head 5 and the holder 63, and determine a position of the holder 63 (light source 6) with respect to the discharge head 5. For this reason, a plurality of protrusions 63c can be provided. In this case, since heat is easily transferred to the protrusions 63c, when the number of protrusions 63c is excessively increased, the heat insulating effect may be reduced. For this reason, the number and interval of the protrusions 63c can be appropriately changed according to the size of the discharge head 5 or the holder 63 and the temperature of the fluid 301a.

Further, it is preferable that the area of a portion of the protrusion 63c coming into contact with the discharge head 5 is reduced. When the area of the portion of the protrusion 63c coming into contact with the discharge head 5 is small, it is possible to suppress heat propagation through the protrusion 63c. For example, as illustrated in FIG. 2A, when the protrusion 63c having a hemispherical shape is used, the protrusion 63c and the discharge head 5 can be brought into point contact with each other, and thus heat propagation can be suppressed.

Further, a shape of the protrusion may be, for example, a tapered shape, a stepped shape, a shape in which one side face is inclined, etc. The tapered shape can be, for example, a cone, a truncated cone, a pyramid, a truncated pyramid, etc.

That is, in a direction orthogonal to a direction from the holder 63 toward the discharge head 5 (axial direction of the protrusion), the cross-sectional area of the protrusion on the tip side may be smaller than the cross-sectional area of the protrusion on the root side.

As illustrated in FIG. 2B, a protrusion 5e can be provided on the discharge head 5, and a tip of the protrusion 5e can be brought into contact with the holder 63. That is, the heat insulating portion can be at least one protrusion 5e provided on the discharge head 5. In this way, it is possible to provide a region containing gas between the discharge head 5 and the holder 63. Since the action, effect, number, interval, shape, etc. of protrusions 5e can be similar to those of the protrusions 63c described above, detailed description thereof will be omitted.

Further, as illustrated in FIG. 2C, the protrusion 63c can be provided on the holder 63, and the protrusion 5e can be provided on the discharge head 5. In this way, it is possible to provide a space (heat insulating portion 10a) between the discharge head 5 and the holder 63. It may be difficult to form the protrusion 63c depending on the arrangement position of the protrusion 63c. It may be difficult to form the protrusion 5e depending on the arrangement position of the protrusion 5e. In this case, the protrusion 5e and the protrusion 63c may be selected and provided according to the ease of formation, etc.

FIG. 3 is a table for showing the effect of the heat insulating portion 10a.

The temperature of the fluid 301a is 60° C., and the flow rate of the fluid 301a is 2 L/min. The electric power applied to one light-emitting element 61 is 2.1 W. A measurement temperature is a temperature Ts of a soldered portion between the light-emitting element 61 and the wiring pattern. In addition, air is supplied to the holder 63 by the cooling portion 8.

A comparative example is a case where the heat insulating portion 10a is not provided, that is, a case where the holder 63 is in contact with the discharge head 5.

An example is a case where a space (heat insulating portion 10a) is provided between the discharge head 5 and the holder 63. The distance between the discharge head 5 and the holder 63 is 2 mm.

As can be seen from FIG. 3, when the space (heat insulating portion 10a) is provided between the discharge head 5 and the holder 63, the temperature Ts of the soldered portion can be lowered by about 30%. This means that it is possible to inhibit the temperature of the light-emitting element 61 from exceeding the maximum junction temperature.

As described above, the fluid sterilization apparatus 1 according to the present embodiment can suppress the temperature rise of the light source 6 (light-emitting element 61) using a simple configuration.

For this reason, when the fluid sterilization apparatus 1 according to the present embodiment is adopted, it is possible to suppress occurrence of a luminous flux drop, non-lighting, etc. or shortening of the life of the light-emitting element 61. Further, since the heat insulating portions 10 and 10a can have a simple configuration, the fluid sterilization apparatus 1 does not increase in size or cost.

(Fluid Sterilization System 100)

Figure 4:
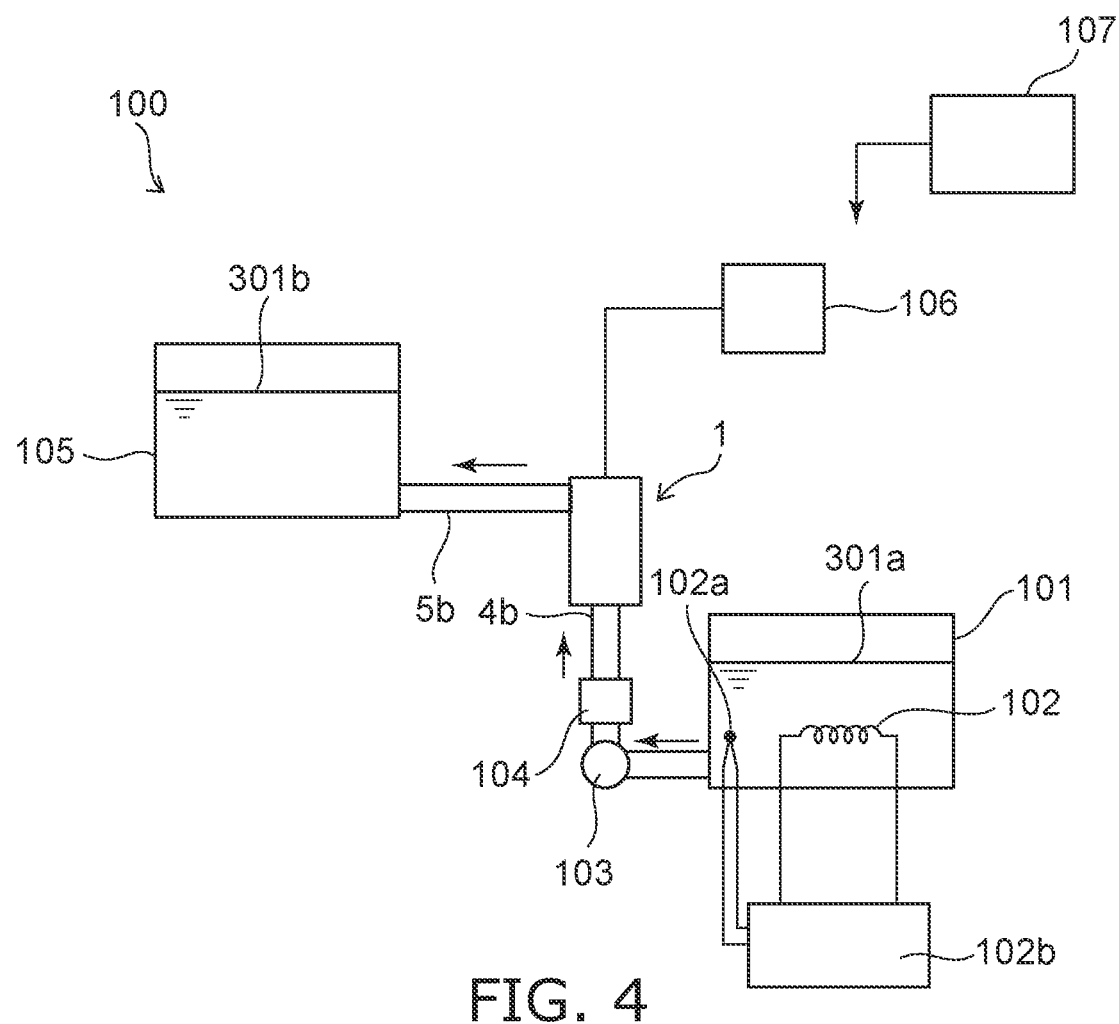
FIG. 4 is a schematic view for illustrating a fluid sterilization system according to the present embodiment.

FIG. 4 is a schematic view for illustrating a fluid sterilization system 100 according to the present embodiment.

As illustrated in FIG. 4, the fluid sterilization system 100 can include the fluid sterilization apparatus 1, the tank 101, the heater 102, the pump 103, the flow rate control valve 104, the tank 105, a power supply 106, and a controller 107.

The tank 101 can store the fluid 301a before sterilization. A discharge port of the tank 101 and the supply port 4a1 of the fluid sterilization apparatus 1 can be connected via, for example, a pipe.

The heater 102 can be provided in the tank 101. Note that the heater 102 can be provided in the pipe between the tank 101 and the fluid sterilization apparatus 1. The heater 102 is not particularly limited as long as the heater 102 can heat the fluid 301a. The heater 102 can utilize, for example, Joule heat or heat from combustion. The heater 102 is electrically connected to a temperature controller 102b. The temperature controller 102b can control the heater 102, for example, based on a signal from a temperature sensor 102a that measures the temperature of the fluid 301a. The temperature controller 102b can control the heater 102 so that the temperature of the fluid 301a becomes, for example, about 40° C. to 90° C.

The pump 103 can be provided in a pipe between the heater 102 and the fluid sterilization apparatus 1. The pump 103 supplies the fluid 301a stored in the tank 101 to the fluid sterilization apparatus 1. Note that even though a case where the tank 101, the heater 102, and the pump 103 are provided is illustrated, for example, the fluid sterilization apparatus 1 may be connected to a factory pipe, etc. for supplying the fluid 301a having a high temperature. That is, it is preferable to provide a fluid supply portion that supplies the fluid 301a having a higher temperature than room temperature (25° C.) (for example, the fluid 301a having a temperature of 40° C. or higher) to the fluid sterilization apparatus 1.

The flow rate control valve 104 can be provided in a pipe between the pump 103 and the fluid sterilization apparatus 1. The flow rate control valve 104 controls the flow rate of the fluid 301a supplied to the fluid sterilization apparatus 1. Further, the flow rate control valve 104 can start and stop the supply of the fluid 301a.

Further, a filter, etc. can be appropriately provided in the supply head 4 of the fluid sterilization apparatus 1 or a pipe connected to the supply port 4a1.

The tank 105 can be connected to the discharge port 5a1 of the fluid sterilization apparatus 1 via a pipe. The tank 105 can store the fluid 301b after sterilization (for example, water). Note that even though a case where the fluid 301b after sterilization is stored in the tank 105 is illustrated, the discharge port 5a1 of the fluid sterilization apparatus 1 may be connected to a device such as a cleaning device that uses the fluid 301b. Further, the fluid 301b discharged from the discharge port 5a1 of the fluid sterilization apparatus 1 may be flushed to an object such as a board.

The power supply 106 is electrically connected to the light source 6 (light-emitting element 61) of the fluid sterilization apparatus 1. The power supply 106 supplies predetermined electric power to the light source 6 (light-emitting element 61). The power supply 106 can be, for example, a DC power supply. The DC power supply may be provided with a rectifying circuit, a converter, a switch, etc. The rectifying circuit is electrically connected to an AC power supply. For example, the rectifying circuit can full-wave rectify an AC voltage applied by the AC power supply. For example, the rectifying circuit may include a diode bridge, etc. The converter converts the voltage full-wave rectified by the rectifying circuit into a predetermined DC voltage. For example, the converter may include a switching circuit. The switch switches between applying electric power to the light source 6 (light-emitting element 61) and stopping the application of electric power.

For example, the controller 107 may include an arithmetic element such as a central processing unit (CPU) and a storage element such as a semiconductor memory. The controller 107 can be, for example, a computer. The storage element can store a control program that controls an operation of each element provided in the fluid sterilization system 100. The arithmetic element controls the operation of each element provided in the fluid sterilization system 100 using the control program stored in the storage element, data input by an operator, etc.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions. Moreover, above-mentioned embodiments can be combined mutually and can be carried out.

What is claimed is:

1. A fluid sterilization apparatus comprising:
   a tubular portion;
   a supply head provided at one end of the tubular portion;
   a discharge head provided at the other end of the tubular portion;
   a holder provided on the discharge head;
   a window provided on the discharge head, one surface of the window being exposed to a flow path provided in the discharge head;
   a board provided on a surface of the holder on a side of the window;
   a light-emitting element provided on the board and allowed to irradiate the window with ultraviolet rays; and
   a heat insulating portion which is provided between the discharge head and the holder and has a lower thermal conductivity than a thermal conductivity of the holder,
   wherein the heat insulating portion is at least one protrusion provided on the holder, and
   a tip of the protrusion is in contact with the discharge head.

2. The apparatus according to claim 1, wherein the holder is detachably provided on the discharge head.

3. The apparatus according to claim 1,
   wherein a space is provided between the window and the light-emitting element, and
   the heat insulating portion contains air.

4. The apparatus according to claim 3,
   wherein the heat insulating portion has at least one of a hole and a groove, and
   the hole and the groove are filled with the air.

5. The apparatus according to claim 1, wherein the protrusion maintains a space between the discharge head and the holder.

6. The apparatus according to claim 1, wherein the protrusion determines a position of the holder with respect to the discharge head.

7. The apparatus according to claim 1, wherein a cross-sectional area of the protrusion on a side of the tip is smaller than a cross-sectional area of the protrusion on a side of a root in a direction orthogonal to a direction from the holder toward the discharge head.

8. The apparatus according to claim 1, wherein a shape of the protrusion is at least one of a tapered shape, a stepped shape, and a shape in which one side face is inclined.

9. The apparatus according to claim 1, wherein a shape of the protrusion is one of a hemisphere, a cone, a truncated cone, a pyramid, and a truncated pyramid.

10. A fluid sterilization apparatus comprising:
    a tubular portion;
    a supply head provided at one end of the tubular portion;
    a discharge head provided at the other end of the tubular portion;
    a holder provided on the discharge head;
    a window provided on the discharge head, one surface of the window being exposed to a flow path provided in the discharge head;
    a board provided on a surface of the holder on a side of the window;
    a light-emitting element provided on the board and allowed to irradiate the window with ultraviolet rays; and
    a heat insulating portion which is provided between the discharge head and the holder and has a lower thermal conductivity than a thermal conductivity of the holder,
    wherein the heat insulating portion is at least one protrusion provided on the discharge head, and
    a tip of the protrusion is in contact with the holder.

11. The apparatus according to claim 10, wherein the protrusion maintains a space between the discharge head and the holder.

12. The apparatus according to claim 10, wherein the protrusion determines a position of the holder with respect to the discharge head.

13. The apparatus according to claim 10, wherein a cross-sectional area of the protrusion on a side of the tip is smaller than a cross-sectional area of the protrusion on a side of a root in a direction orthogonal to a direction from the holder toward the discharge head.

14. The apparatus according to claim 10, wherein a shape of the protrusion is at least one of a tapered shape, a stepped shape, and a shape in which one side is inclined.

15. The apparatus according to claim 10, wherein a shape of the protrusion is one of a hemisphere, a cone, a truncated cone, a pyramid, and a truncated pyramid.

16. The apparatus according to claim 1, wherein the heat insulating portion contains a resin.

17. The apparatus according to claim 16, wherein the resin is at least one of a phenol resin and a fluororesin.

18. The apparatus according to claim 1, wherein a thickness of the heat insulating portion is 1 mm or more and 3 mm or less.

19. A fluid sterilization system comprising:
the fluid sterilization apparatus according to claim 1; and
a fluid supply portion capable of supplying a fluid having a higher temperature than room temperature to the supply head of the fluid sterilization apparatus.

20. A fluid sterilization system comprising:
the fluid sterilization apparatus according to claim 10; and
a fluid supply portion capable of supplying a fluid having a higher temperature than room temperature to the supply head of the fluid sterilization apparatus.

* * * * *